US012661489B1

(12) United States Patent
Hall et al.

(10) Patent No.: US 12,661,489 B1
(45) Date of Patent: Jun. 23, 2026

(54) MEDICAL APPLICATOR

(71) Applicant: Primus Pharmaceuticals, Inc.,
Scottsdale, AZ (US)

(72) Inventors: Trevor T. Hall, Scottsdale, AZ (US);
Ryan E. Hartung, Scottsdale, AZ (US);
James D. Weir, Scottsdale, AZ (US)

(73) Assignee: Primus Pharmaceuticals, Inc.,
Scottsdale, AZ (US)

( * ) Notice: Subject to any disclaimer, the term of this
patent is extended or adjusted under 35
U.S.C. 154(b) by 0 days.

(21) Appl. No.: 19/394,740

(22) Filed: Nov. 19, 2025

(51) Int. Cl.
A61M 35/00 (2006.01)

(52) U.S. Cl.
CPC ... A61M 35/003 (2013.01); A61M 2205/3327
(2013.01); A61M 2210/04 (2013.01)

(58) Field of Classification Search
CPC .............. A61M 35/003; A61M 35/006; A61M
2205/3327; A61M 2210/04
USPC ........................................ 604/290
See application file for complete search history.

(56) References Cited

U.S. PATENT DOCUMENTS

| | | | |
|---|---|---|---|
| 2,233,811 | A | 3/1941 | Doty |
| D271,624 | S | 11/1983 | Paulson |
| 4,483,356 | A | 11/1984 | Kales |
| 5,568,669 | A | 10/1996 | Godown |
| D380,868 | S | 7/1997 | Santore |
| 5,671,497 | A | 9/1997 | Abdo |
| 5,842,488 | A | 12/1998 | Belleau |

| | | | | |
|---|---|---|---|---|
| 5,952,090 | A | * | 9/1999 | Fan ........................... B32B 5/18 |
| | | | | 521/54 |
| 6,415,470 | B1 | * | 7/2002 | Ramrattan ............. A45D 34/04 |
| | | | | 15/209.1 |
| 6,438,787 | B1 | * | 8/2002 | Young .................... A47K 7/028 |
| | | | | 15/210.1 |
| D462,480 | S | | 9/2002 | Jones |
| D467,686 | S | | 12/2002 | Kohler |
| D473,762 | S | | 4/2003 | Kerr |
| D481,270 | S | | 10/2003 | Siegel |
| D487,556 | S | | 3/2004 | Siegel |
| D488,997 | S | | 4/2004 | Angeletta |
| 6,726,385 | B1 | | 4/2004 | Borowski |
| D490,565 | S | | 5/2004 | Ali |
| D497,450 | S | | 10/2004 | Scofield |
| D518,597 | S | | 4/2006 | Sommers |
| 7,185,385 | B2 | | 3/2007 | Kohler |
| D587,844 | S | | 3/2009 | Slavin |
| D606,372 | S | | 12/2009 | Gorskey |
| D631,711 | S | | 2/2011 | Jossem |
| D677,532 | S | | 3/2013 | Joseph |
| 8,646,142 | B2 | | 2/2014 | Ferrara |

(Continued)

FOREIGN PATENT DOCUMENTS

| | | | | |
|---|---|---|---|---|
| AU | 2005100524 | A4 | 6/2005 | |
| GB | 2412573 | A * | 10/2005 | ............... B05C 1/00 |

*Primary Examiner* — Jacqueline F Stephens
(74) *Attorney, Agent, or Firm* — James Rogers; Clark G.
Sullivan

(57) ABSTRACT

An applicator used for spreading compositions such as
ointments, creams, lotions, or foams to a subject's skin or
other external part of the body. The applicator includes a
handle, an extendable and retractable telescopic shaft and a
rectangular, diamond shaped head. In one embodiment, the
rectangular, diamond shaped head includes a center ridge
which serves to define three separate flexible wedge like
surfaces on each side of the head.

21 Claims, 13 Drawing Sheets

(56)         References Cited

U.S. PATENT DOCUMENTS

| | | | |
|---|---|---|---|
| D713,220 S | 9/2014 | Cloutier | |
| 9,119,456 B1 | 9/2015 | Hudson | |
| D747,938 S | 1/2016 | O'Connell | |
| D830,139 S | 10/2018 | Li | |
| D996,927 S | 8/2023 | Zhang | |
| D1,049,800 S | 11/2024 | Yin | |
| 2001/0034920 A1* | 11/2001 | Brown | A47K 7/028 |
| | | | 15/209.1 |
| 2002/0076259 A1 | 6/2002 | Williams | |
| 2004/0071494 A1 | 4/2004 | Staniforth | |
| 2005/0268416 A1 | 12/2005 | Sommers | |
| 2012/0097183 A1 | 4/2012 | Miller | |
| 2012/0177430 A1* | 7/2012 | Ferrara | A45D 34/04 |
| | | | 401/6 |
| 2014/0037360 A1 | 2/2014 | Hofmann | |
| 2014/0070555 A1 | 3/2014 | Rose | |
| 2016/0113375 A1 | 4/2016 | Lim | |
| 2016/0278502 A1 | 9/2016 | McGee | |
| 2018/0325623 A1 | 11/2018 | Kashi | |
| 2019/0218019 A1* | 7/2019 | Beaubien | A61M 35/003 |
| 2020/0121899 A1* | 4/2020 | Fox | A61M 35/003 |
| 2022/0265979 A1 | 8/2022 | Sabherwal | |
| 2022/0369787 A1 | 11/2022 | Lemmerman | |
| 2022/0386754 A1 | 12/2022 | Murray | |
| 2024/0138542 A1 | 5/2024 | Maiga | |

* cited by examiner (Perspective View)

(Side View)

(Top View)

(Back View)

(Front View)

MEDICAL APPLICATOR

BACKGROUND OF THE INVENTION

Various applicators have been described to aid the user for spreading lotions or ointments, particularly in hard-to-reach areas. Such applicators include those of the integral type as for example US 2002/0076259 and U.S. Pat. No. 6,726,385. In order to save space, other applicators include mechanisms for extension and retraction. In this respect, applicators of the telescopic type include for example U.S. Pat. Nos. 4,483,356, 5,568,669, 5,671,497, US 2022/0386754 and US 2012/0177430.

However, none of the applicators described above meet the advantages provided by the applicator disclosed herein with respect to the application of compositions, manipulation, ease of cleaning and multifunctionality.

SUMMARY OF THE INVENTION

In one aspect, the current invention is directed to an applicator in a telescopic and spatula form which is used for the spreading of compositions such as ointments, creams, gels, lotions, or foams on a subject's body such as a human body. The applicator includes a handle, a telescopic shaft and a rectangular, diamond surface head, wherein the handle is configured to completely contain the telescopic shaft when the shaft is in its retracted state and where the telescopic shaft extends longitudinally outward from a distal opening on the handle through a connection collar on the head when in its extended state.

The diamond shaped head profile due to its multiple angle profile offers optimal spreading of compositions. Such compositions can be in the form of ointments, creams, lotions, foams or gels. In a separate embodiment, the rectangular, diamond surface head includes a serrated edge along one of its lengths, which provides even greater functionality for the head of the applicator. In another embodiment, the diamond surface head includes a wavy edge which is configured for easy application to bumpy, cracked or psoriatic skin surfaces.

In a preferred embodiment, the rectangular, diamond shaped head includes a center ridge which serves to define three separate flexible wedge like surfaces on each side of the head, a flexible inverted triangle shaped triangular surface at the tip of the head and two opposing flexible length wedge surfaces which run parallel to the length edges to a bottom width edge and its associated neck collar. The flexible hedged surfaces advantageously allows easier and better application of a gel, lotion or medication.

In a separate embodiment, one of the opposing flexible length wedge length surfaces includes an embossed area which is configured to specify a quantity of a composition such as a lotion, gel, ointment or foam for topical application to the skin. In a further embodiment, the embossed area includes the etched or embossed marking "1 FTU", which stands for one fingertip unit, the length of the embossed area is configured to approximate 1 FTU of the composition.

In a separate embodiment, the surface of the opposing wedge-like surfaces includes the phrase "CLEANSE AFTER USE". In a separate embodiment, the opposing flexible rectangular length edges is a serrated or rounded serrated edge rather than a straight lined edge. In another preferred embodiment, the opposing flexible rectangular length edges is a wavy edge.

The applicator head can be composed of various materials. In one preferred embodiment, the head is composed of an elastomer plastic. In other embodiments the head is composed of a thermoplastic elastomer. In another embodiment the head is composed of silicone.

The telescopic shaft of the applicator can include two or more sections, which can depend on the length desired for extension. In some embodiments, the telescopic shaft includes 2, 3, 4 or 5 sections. Each section of the shaft has a slight taper, meaning one end is slightly wider than the other. In use, when the user extends the shaft, the user pulls one section out from the larger section. The tapered end lodges firmly inside the larger tube, creating a friction lock that holds it in place. For example, if only 2 sections are used for the telescopic shaft, then the handle will be molded to a first base section of the telescopic lens which includes an opening just slightly larger than a second extendable telescopic top shaft portion to create friction to keep the telescopic shafts in place until force is applied to extend the shaft. Each of the shaft sections of the telescopic shaft are configured to permit rotation with respect to each other which advantageously permits the head of the shaft to more easily be rotated for better application of a gel, lotion or medication by a user.

In a preferred embodiment, the telescopic shaft is extendable and includes three sections which includes a base telescopic section which is configured to fit inside the handle of the applicator, a middle section of the telescopic shaft which is configured to fit inside the base shaft section, and a top shaft portion which is configured to fit inside the middle shaft section and which includes an upper portion that fits through a neck collar up to the pinnacle of the inverted triangle of the head of the applicator. In a preferred embodiment, the base telescopic section is molded to the handle and the upper portion of the top shaft portion is molded to the head.

In a preferred embodiment the telescopic shafts are composed of stainless steel. However, other materials can be used, particularly those which are corrosion resistant, such as copper, bronze, aluminum or titanium, or plastic. In some embodiments, the telescopic shafts are composed of a metal.

In some embodiments, the handle of the applicator includes raised ridges which are spaced along the length of the handle so that the length between each ridge defines a length marking used for measuring the size of lesions on the skin. In some embodiments the length markings are equally spaced and measured in centimeters.

In some embodiments, the handle is connected at its proximal end to a base tool. In one embodiment, the base tool is in the shape of a question mark or in the shape of a hook which can be used for hanging and/or storing the applicator. In another embodiment, the base tool is in the form of a fin or a palmate foot which can be used as an additional applicator to the rectangular, diamond shaped head for application of the composition.

In one embodiment the head, handle and/or base tool are translucent or opaque. In other embodiments the head, handle and/or base tool of the applicator are various colors such as blue, green or red. In some embodiments, the head is of one color and the handle and/or base tool are of a second and/or third color.

In a further aspect, the invention provides a kit that includes an applicator in accordance with the invention. Such kits can include various compositions such as ointments, creams, lotions, gels or foams as well as instructions for use of the applicator with said ointment, cream, lotion, gel or foam. The kit will typically include a box to fit each of the components of the kit.

In another aspect, the invention includes methods of applying compositions such as a gel, lotion, foam or ointment to the skin or other external part of the body of a subject such as a human using the applicator in accordance with the invention for the treatment of a skin disorder. In some embodiments, the composition is a pharmaceutical composition. In some embodiments, the skin disorder is selected from the group of acne, eczema (atopic dermatitis), psoriasis, rosacea, contact dermatitis, and other abnormal and or dry skin conditions. In other embodiments, the skin disorder is selected from the group of warts, seborrheic dermatitis, hives, and various skin cancers.

In one preferred embodiment, the method of application includes the steps of: a) grasping the handle of an applicator as described herein, b) extending the telescopic shaft to a desired length, (c) dispensing an amount of medicament to mirror the embossed area located on a wedged length surface of the rectangular diamond head surface, and (c) manipulating the applicator to apply the medicament onto the bodily surface.

DETAILED DESCRIPTION OF THE INVENTION

Figure 1:
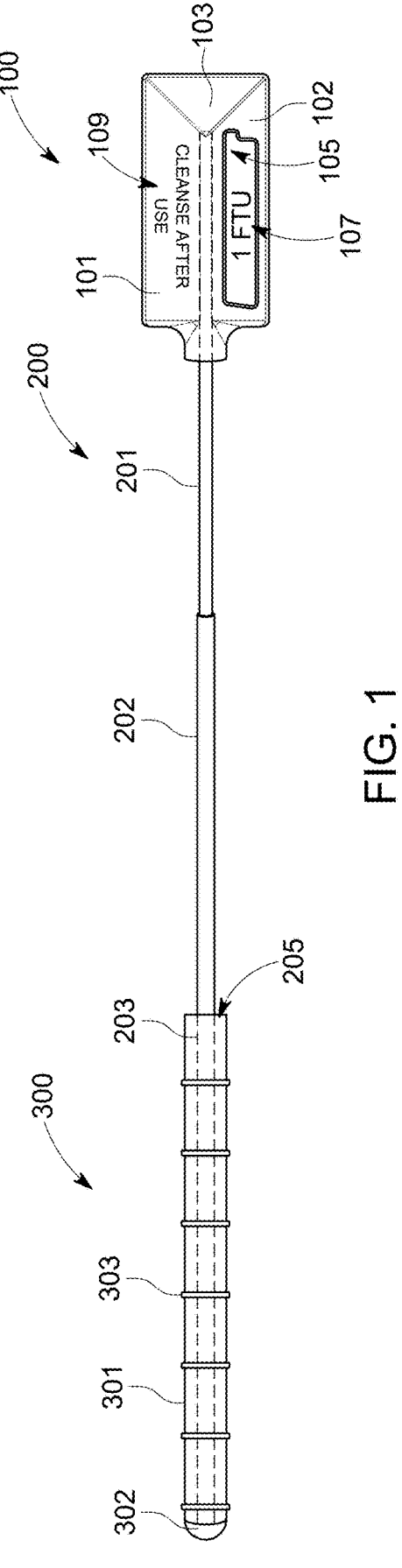
FIG. 1: shows an extended perspective view of the applicator, showing a silicone head having a rectangular, diamond surface and telescoping rod assembly, according to a preferred embodiment of the invention.

Many individuals manually apply lotions, creams and oils to themselves or to others to provide skin protection, rejuvenation and treatment. Such lotions, creams and oils are often applied to skin surfaces with bare hands, a clean cloth, cotton woold or gauze. To aid in their application, various applicators have been designed to aid in the application of such compositions. For example, US 2002/0076259 discloses a disposable lotion applicator having a generally flat, elongated body member made out of an absorbent, flexible material that is suitable for receiving and retaining lotion. Lotion can be applied to the applicator and the user of the applicator can apply lotion by grasping the ends of the applicator to rub the lotion across hard-to-reach areas of the body. U.S. Pat. No. 2,233,811 also discloses an applicator for applying certain ointments or creams to the human body which includes a handle which is integrally formed with a spatulate member terminating in a convex transversely disposed spreading surface. U.S. Pat. No. 6,726,385 also discloses a handled device which aids one in applying lotion or sun-screen to their back region and other hard-to-reach areas which includes a long handle portion which includes an elongated handle that supports a head with a flat applicator pad constructed of a sponge-like material.

In addition to the integral design, various applicators have been designed which include a telescopic mechanism to not only add extension to the applicator but also allow retraction. In this respect, U.S. Pat. No. 4,483,356 discloses a lotion applicator which employs a length adjustable handle which is inserted into a flexible bale with a pad attached which adjustably swivels so that the flattened pad remains in contact with the user's skin. U.S. Pat. No. 5,568,669 also discloses an applicator for use in applying lotion that includes a housing, a handle and an applicator pad. The applicator pad is attached to the housing and is used to spread lotion. The housing is hollow so as to receive the handle when the handle is being stored. U.S. Pat. No. 5,671,497 also discloses an applicator for applying substances to hard-to-reach portions of a user's body which includes a handle configured to be gripped by a user at one end, a second opposite end, an attachment portion carried by the second end and a pad removably attachable to the attachment portion. The handle includes a rigid portion extending form a first end to an opposite end portion, a sleeve having an axial opening into which the opposite end portion is received and a bendable portion having opposite end portions received into the axial opening. US 2022/ 0386754 further discloses a device to apply lotion or cream to an individual's back which includes a reversible lotion applicator head, main handle, threaded lock collar for extending the handle and locking the handle in place, and an extendable scratch handle.

US 2012/0177430 further discloses an applicator that includes a head section and a handle assembly having a shank and a gripper. The shank is telescopic providing an extended length of about 12 inches and a retractable length of about 8.5 inches. The head assembly can include a socket and ball providing rotational means. The applicator is useable by the user to apply oil, lotion and cream to the bodily skin surface in hard-to-reach locations.

None of the patents/publications above disclose an applicator as herein described where the telescopic shaft of the applicator is received and fits into the handle, nor do any of these patents disclose an applicator having a rectangular, diamond shaped head or other features which add to the functionality of the applicator as herein described.

Medical compositions for application to the skin typically are typically available in formulations such as ointments, creams, lotions, gels, foams, oils, solutions, and shampoos. Topical corticosteroids for example are an essential tool for treating inflammatory skin conditions such as psoriasis and atopic dermatitis. Topical corticosteroids are classified by strength and the risk of adverse effects such as atrophy, striae, rosacea, telangiectasias, purpura, and other cutaneous and systemic reactions. The risk of adverse effects increases with prolonged use, a large area of application, higher potency, occlusion, and application to areas of thinner skin such as the face and genitals. The quantity of corticosteroid prescribed depends on the duration of treatment, the frequency of application, the skin location, and the total surface area treated. Correct patient application is critical to successful use. (McEleney, "Topical Corticosteroids: Choice and Application" Am Fam Physician. 2021; 103 (6): 337-343).

According with skin conditions such as psoriasis, special consideration with the respect to the correct amount or dosage of medicine must be considered. A major cause of patients failing to comply with appropriate treatment regimens for the administration of therapeutic agents to the skin, is that they find it difficult to measure out precise amounts of conventional topical formulation. One method of measuring the correct amount of a therapeutic agent to be applied to a patient's skin via a topical formulation is to instruct the patient to squeeze the topical formulation from a dispenser, such as a tube, along an index finger starting at the fingertip down to the first joint. The amount of therapeutic agent thus measured has become known as one fingertip unit (FTU). Patients may be taught application using the fingertip unit method. One fingertip unit is the amount of medication dispensed from the tip of the index finger to the crease of the distal interphalangeal joint and covers approximately 2% body surface area on an adult. (McEleney, "Topical Corticosteroids: Choice and Application" Am Fam Physician. 2021; 103 (6): 337-343).

The fingertip application method for topical ointments has several disadvantages, including inconsistent dosing, risk of cross-contamination, and absorption issues in specific body areas. Because the FTU relies on a non-standardized tool—the patient's finger—the actual amount of steroid applied can vary greatly. This can lead to either under- or over-application of the medication.

US20220265979 discloses applicator heads for administration of a topical formulation. The applicator head includes an outlet opening which is connected or connectable to a flow conduit formed inside the applicator head. When the applicator head is used with a package for topical formulation, the topical formulation can be urged through the flow conduit and out of the outlet opening. The publication does not disclose dosage measuring devices which are part of the types of heads described herein according to the current invention.

US 2004/0071494 discloses an applicator for applying a spreadable composition to the skin that includes a receiving means for carrying a unit or measured dose of the composition. In one embodiment, the applicator includes a portion coupled to the unit dose and a second portion that is generally cylindrical in shape which is configured to fit around a finger of the user to aid in holding the applicator and spreading the unit dose on the desire skin region (see FIGS. 2a-2b). The publication does not disclose the configurations for a fingertip measuring dose structure as herein described nor does the publication disclose including a fingertip measuring structure as part of an extendable or multi-functional applicator as described for the current invention.

In addition to the precise dose of the medicament, some diseases present even more special considerations. For example, psoriasis is a chronic, inflammatory autoimmune skin disease affected by genetic and various environmental factors. It has been recognized as a significant public health burden. (Guo, "Advances in the pathogenesis of psoriasis: from keratinocyte perspective" Cell Death and Disease (2022) 13:81)

Psoriatic plaque thickness is a clinical measure of psoriasis severity. It is important to measure the depth (or thickness) of psoriasis plaques for determining disease severity, monitoring treatment effectiveness, and understanding the biological differences between patients. In clinical practice, plaque thickness is a key component of standard evaluation metrics. (Kreuger, "Observations of Psoriasis in the Absence of Therapeutic Intervention Identifies Two Unappreciated Morphologic Variants, Thin-Plaque and Thick-Plaque Psoriasis, and their Associated Phenotypes" Journal of Investigative Dermatology (2006) 126, 2397-2403)

The applicator as herein described can include ridges on the handle of the applicator which define precise marking lengths used for accurately measuring the length or thickness of lesions associated with skin diseases such as psoriasis.

Referring now to the figures, FIG. 1 shows a perspective view of an applicator according to a preferred embodiment of the invention. Applicator includes a head 100 and a handle 300 which is configured to house an extendable telescopic shaft 200 which extends longitudinally outward from a distal opening 205 of a base shaft 203. In the embodiment shown, telescopic shaft 200 includes three shafts, the base shaft 203 which is enclosed inside handle 300, a middle shaft 202 and a top portion shaft 201 which includes a top portion 208 that extends into head 100.

Figure 7:
FIG. 7: illustrates a front view of the having a rectangular, diamond shaped head with one of the head lengths having a serrated edge and its surface area on one of its wedge-like surface length area just above the serrate edge including the lettering "CLEANSE AFTER USE". The opposing length side of the rectangle shows a straight length edge includes an indented rectangular, curved shaped region which is configured to precisely measure 1 fingertip unit of medicament along with the words "1 FTU" etched or embossed into the wedge-like surface area.
Figure 7:
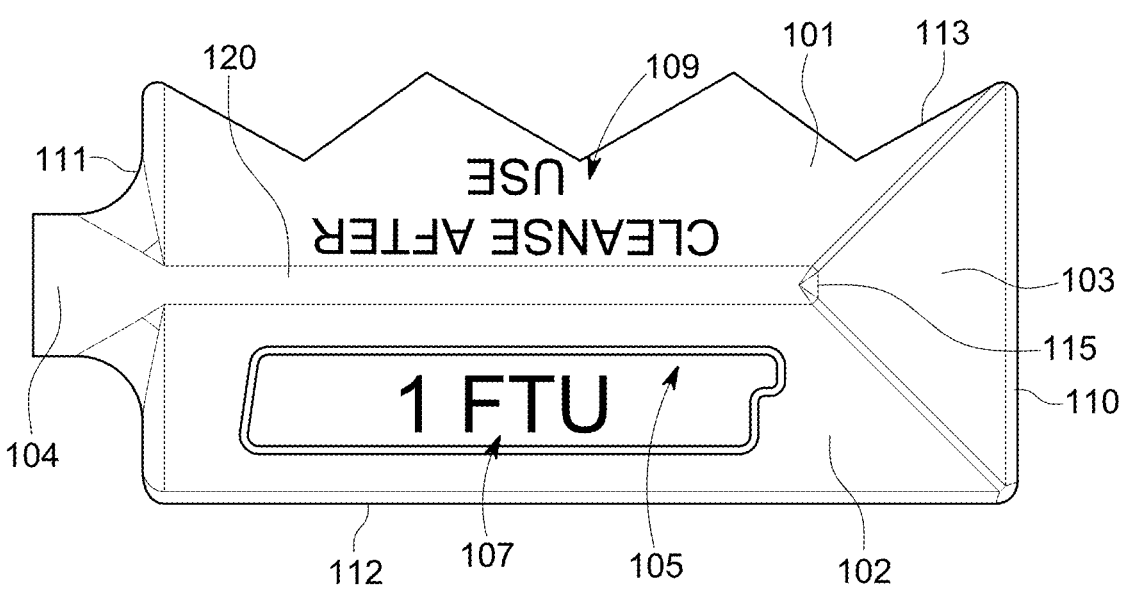

As most clearly shown in FIG. 7, the head 100 of the applicator is of a rectangular, diamond shape that includes a top width side 110, two opposing perpendicular length sides 112, 113 and a base width side 111, which meets collar 104. The top width side 110 of the head 100 serves as a base of an inverted triangle which meets at a pinnacle 115 of the inverted triangle so that it defines a flexible, inverted triangular shallow hedge top surface 103 on each side of the head of the applicator. Running from the pinnacle 115 of the inverted triangle is a central ridge 120 which runs parallel to the opposing perpendicular lengths sides 112, 113 of the head 100 until it meets the base width side 111 and a collar 104 which is connected to the base width side 111.

The center ridge 105, collar 104, opposing base widths 110, 111, opposing length sides 112, 113 and top sides of the inverted triangle define a first wedge like surface 101 on one side of the central ridge 120 and an opposing second flexible wedge length surface 102 on the opposing side of the central ride 105. The flexible hedged opposing surfaces 101, 102 on each side of head 100 advantageously allows easier and better application of a gel, lotion or medication to the skin of a subject, particularly when used in conjunction with the flexible triangular hedge top width surface 103.

In the preferred embodiment shown in FIG. 1, the head further includes the etched phrase "CLEANSE AFTER USE" 109 which are embossed into one the wedge width length surfaces 101. The opposing wedge length surface 102 further includes an embossed area 105 which is configured to approximate a finger-tip unit volume for a composition such as a lotion, gel, foam, or ointment for topical application to the skin. The term "approximate" is defined to be within 10% of the actual intended volume. In the embodiment shown in FIG. 1, the surface of the embossed area 105 includes the embossed marking "1 FTU" 107.

The applicator head 100 can be composed of various materials. In one preferred embodiment, the head is composed of an elastomer plastic. In other embodiments the head is composed of a thermoplastic elastomer. In another embodiment, the head is composed of silicone.

In the preferred embodiment shown in FIG. 1, the telescopic shaft 200 is shown in a fully extended position and includes three sections; a base telescopic section 203 which is configured to fit inside the handle 300 of the applicator, a middle shaft section 202 which is configured to fit inside the base shaft section 203, and a top shaft portion 201 which includes an upper portion 208 that fits through a neck collar 104 and into head 100 up to the pinnacle 115 of the inverted triangle of flexible triangular hedge top width surface 103.

In a preferred embodiment, the base telescopic section 203 is secured by molding to handle 300. The upper telescopic section 208 is secured by molding to the central ridge of head 100.

In a preferred embodiment the telescopic shafts are composed of stainless steel. However, other materials can be used, particularly those which are corrosion resistant, such as copper, bronze, aluminum or titanium. In some embodiments, the telescopic shafts are composed of a metal.

While the preferred embodiment in FIG. 1 illustrates a telescopic shaft with 3 shaft portions, other shaft numbers are possible. For example, in some embodiments, the telescopic shaft includes 2, 4 or 5 sections (not shown). As with the three shaft version shown in FIG. 1, each section of the shaft has a slight taper, meaning one end is slightly wider than the other. In use, when the user extends the shaft, the user pulls one section out from the larger section. The tapered end lodges firmly inside the larger tube, creating a friction lock that holds it in place until force is used to put it out or it is fully extended. For example, if only 2 sections are used for the telescopic shaft, then the handle will be molded to a first base section of the telescopic lens which includes an opening just slightly larger than a second extendable telescopic top shaft portion to create friction to keep the telescopic shafts in place until force is applied to extend the shaft.

Each of the shaft sections of the telescopic shaft are configured to permit rotation with respect to each other which advantageously permits the head 100 of the applicator to more easily be rotated for quicker and easier application of a gel, lotion or medication by a user. The base shaft 203 which sits in the handle 300 can also be rotated along with the handle which may also aid in manipulation of the applicator.

In the preferred embodiment shown in FIG. 1, handle 300 further includes raised ridges 303 which are spaced along the length 301 of handle 300 so that the length between each ridge defines correspond to a measurement used for measuring the size of lesions on the skin of a subject. In some embodiments the length markings are equally spaced and measured in center meters.

Figure 2:
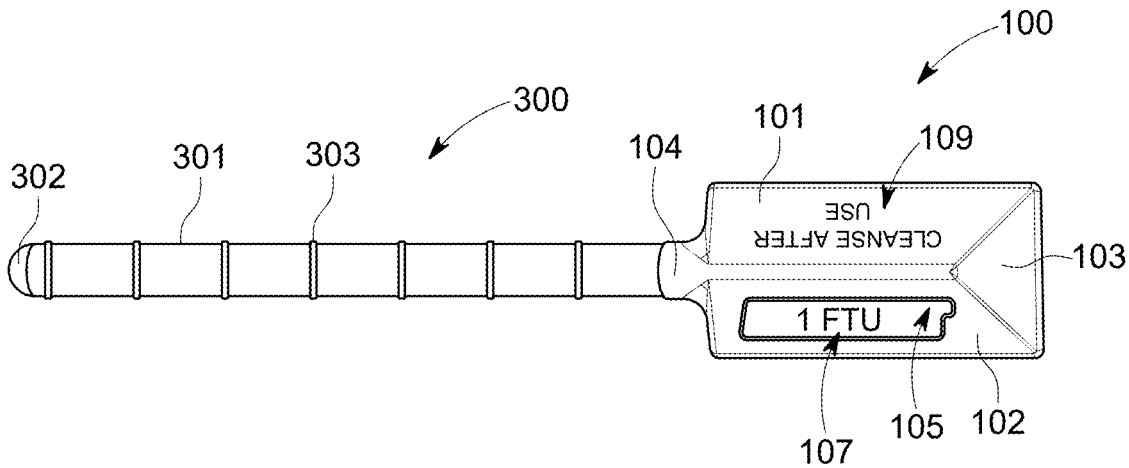
FIG. 2: shows a retracted side view of the applicator, according to a preferred embodiment of the invention.

FIG. 2 shows a retracted side view of the applicator, according to a preferred embodiment of the invention. The figure shows that collar 104 sits flush up against the distal opening 205 (see FIG. 1) of handle 300.

Figure 3:
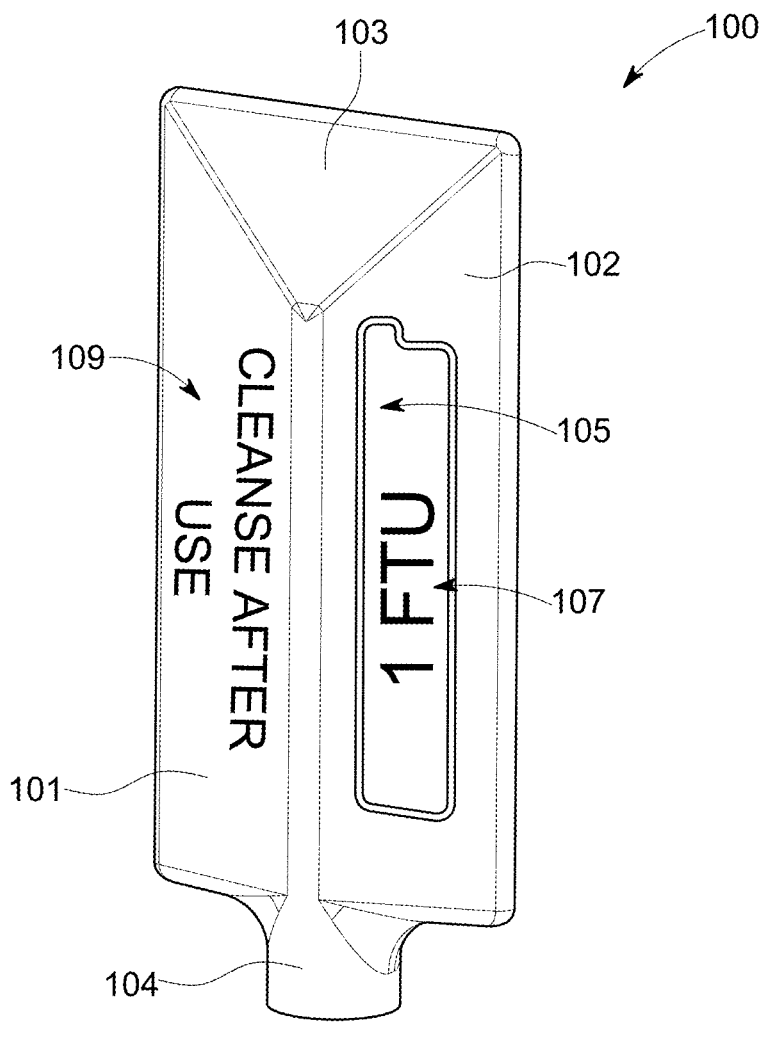
FIG. 3: shows a perspective view of the head of the applicator according to a preferred embodiment of the invention.
Figure 4:
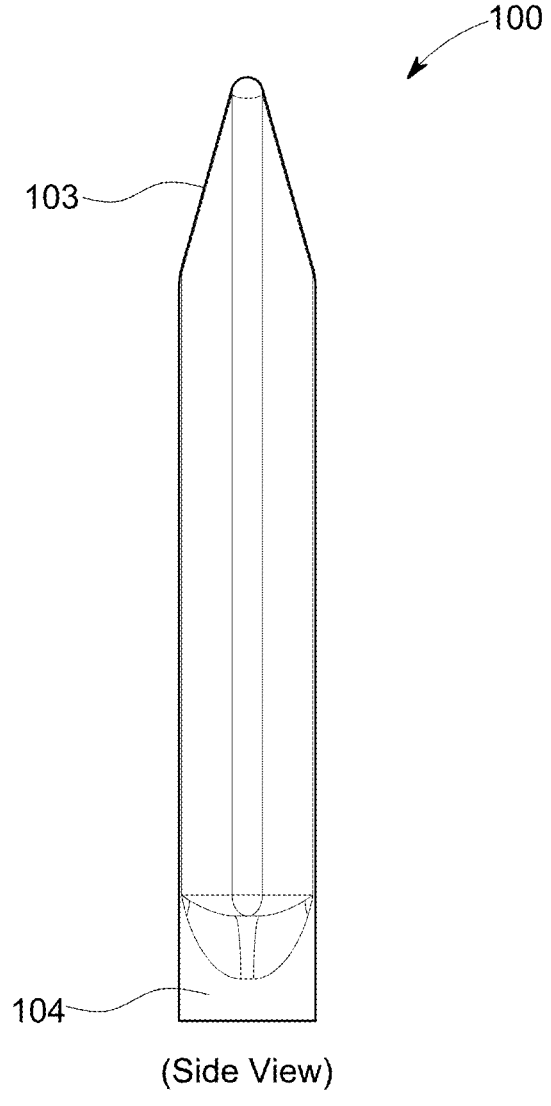
FIG. 4: shows a side view of the head of the applicator having a rectangular, diamond shaped surface head, according to a preferred embodiment of the invention. The side view shows a thin, wedge-like cross-section of the rectangular head, with rounded edges and a central ridge that forms its diamond-like front surface.
Figure 5:
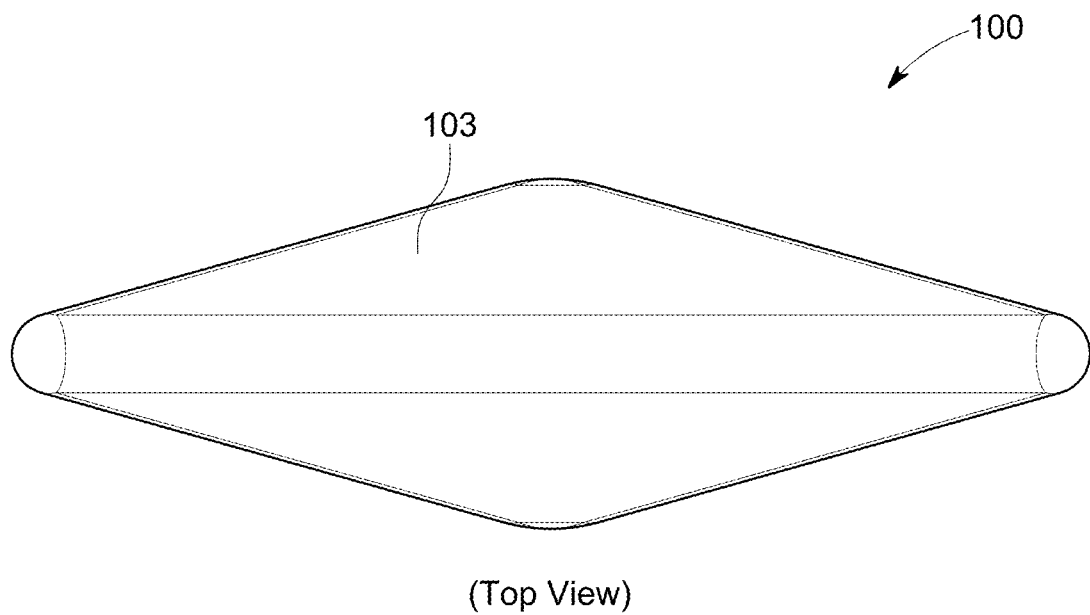
FIG. 5 shows a top view of the applicator head having a rectangular, diamond shaped surfaced head, according to a preferred embodiment of the invention.

FIG. 3-5 are perspective, side and top views of head 100, according to a preferred embodiment of the invention.

Figure 6:
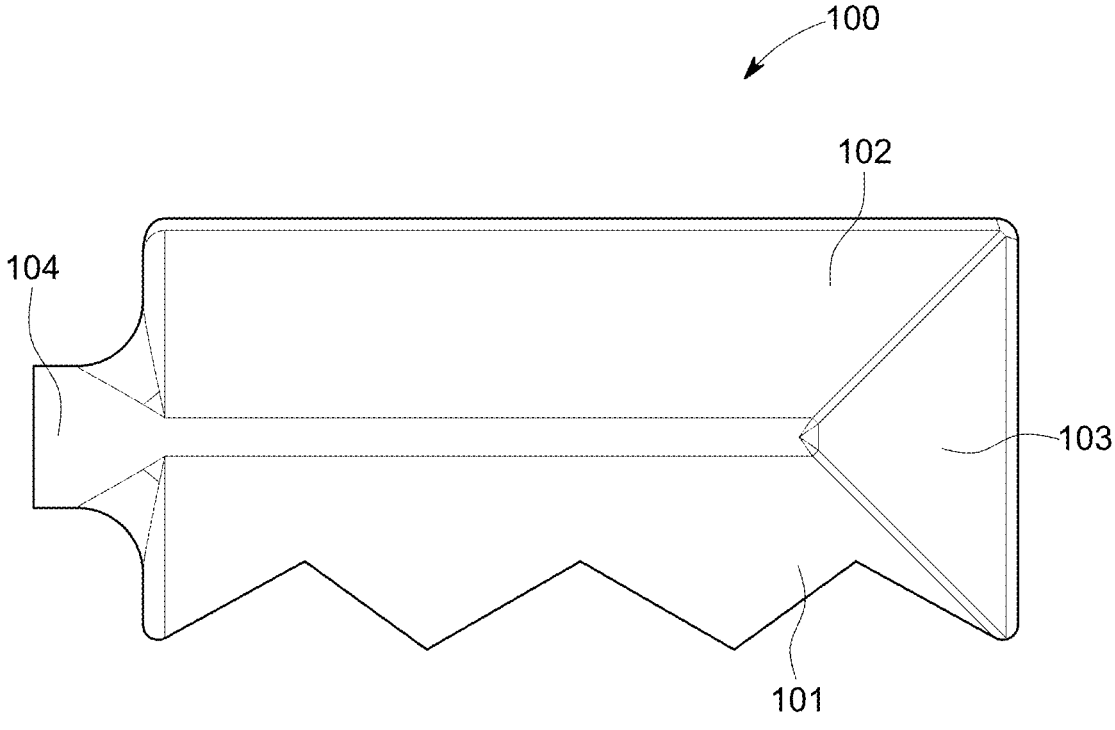
FIG. 6: shows a back view of the applicator having a rectangular, diamond shaped surfaced head with one of the longer sides of the rectangular head having been replaced with a serrated edge, according to a preferred embodiment of the invention.

FIGS. 6-7 illustrate back and front views of an additional embodiment of the head where in this particular embodiment the first flexible wedge length surface 101 includes a serrated length edge 113, which can provide additional functionality to head 100 with respect to ease of spreading ability of head 100.

Figure 8:
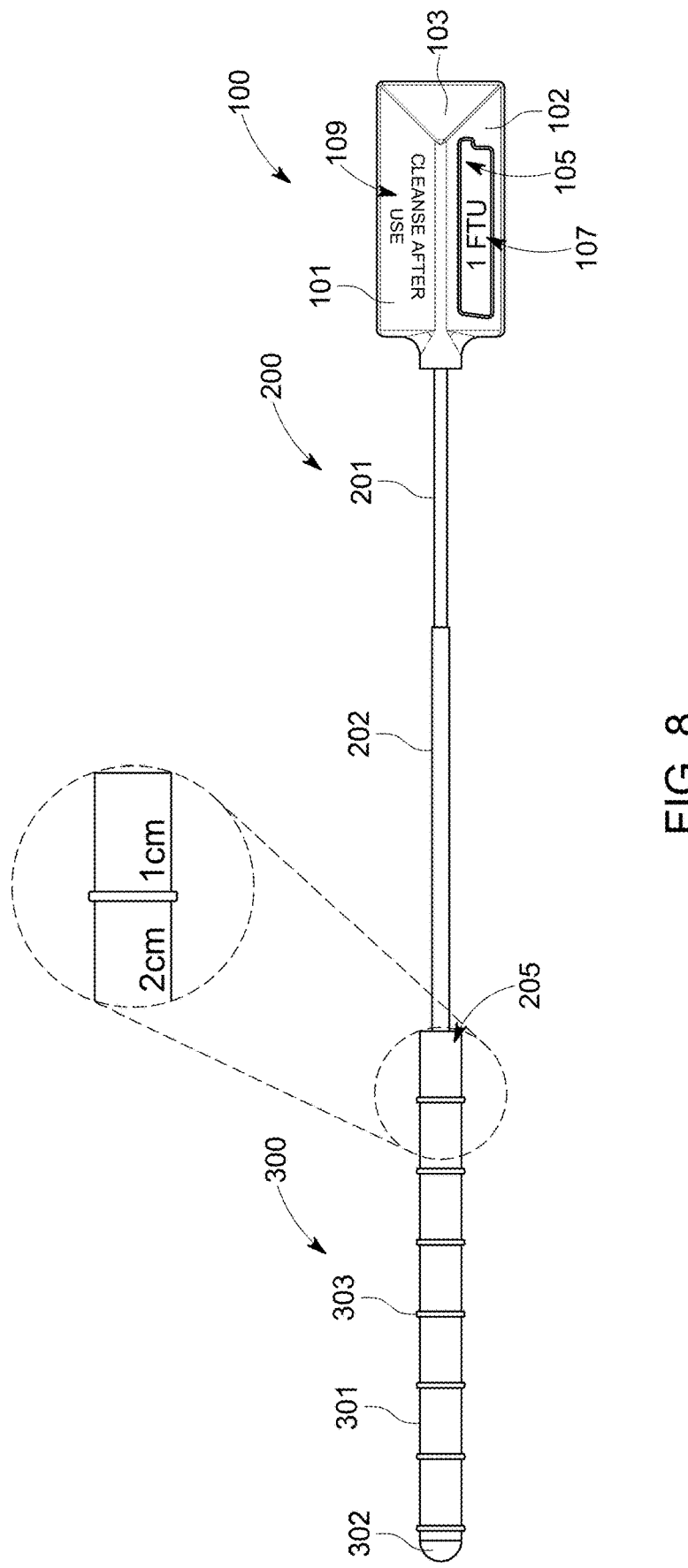
FIG. 8: shows an extended perspective view of the applicator, showing a silicone head having a rectangular, diamond surface and telescoping rod assembly, according to a preferred embodiment of the invention. In the embodiment shown, the handle includes raised unit markings for measuring the depth or length of lesions. In the embodiment shown, the length of each marking is 1 cm.

FIG. 8 illustrates a preferred embodiment of the applicator with telescopic shaft 200 in its extended position which includes handle 300 that includes ridges 303 along length 301. As shown in the embodiment of FIG. 8, measurement is in centimeters (cm) starting from distal opening 205 of handle 300 where the distance from the distal opening of head 300 to a first ridge is 1 cm and the next distance between the first and second ridges is 2 cm. While the figure shows equal lengths between each ridge, other lengths and markings are possible.

Figure 9:
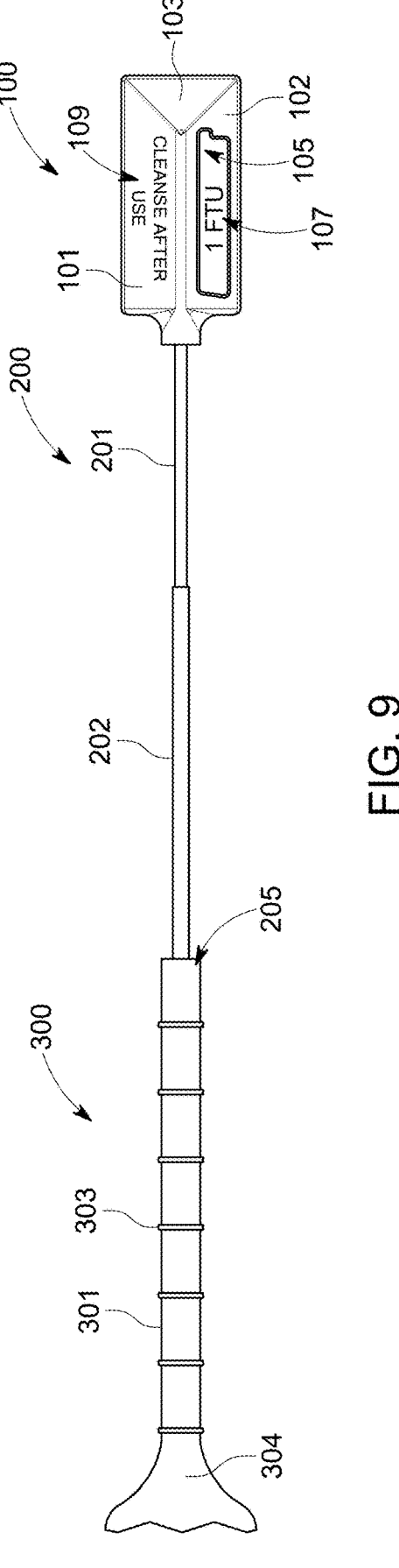
FIG. 9: shows an extended perspective view of the applicator, showing a silicone head having a rectangular, diamond surface and telescoping rod assembly, according to a preferred embodiment of the invention. In the embodiment shown, the handle includes raised fingertip unit markings for measuring the depth of lesions and further includes a base tool attached at its base which resembles a fin and includes a serrated edge.

FIG. 9 illustrates a preferred embodiment of the applicator with telescopic shaft 200 in its extended position which includes base a tool 304, resembling a fin, attached to the proximal end of handle 300 which in this embodiment includes a serrated edge. The base tool 304 with serrated edge provides dual functionality in addition to diamond shaped head 100.

Figure 10:
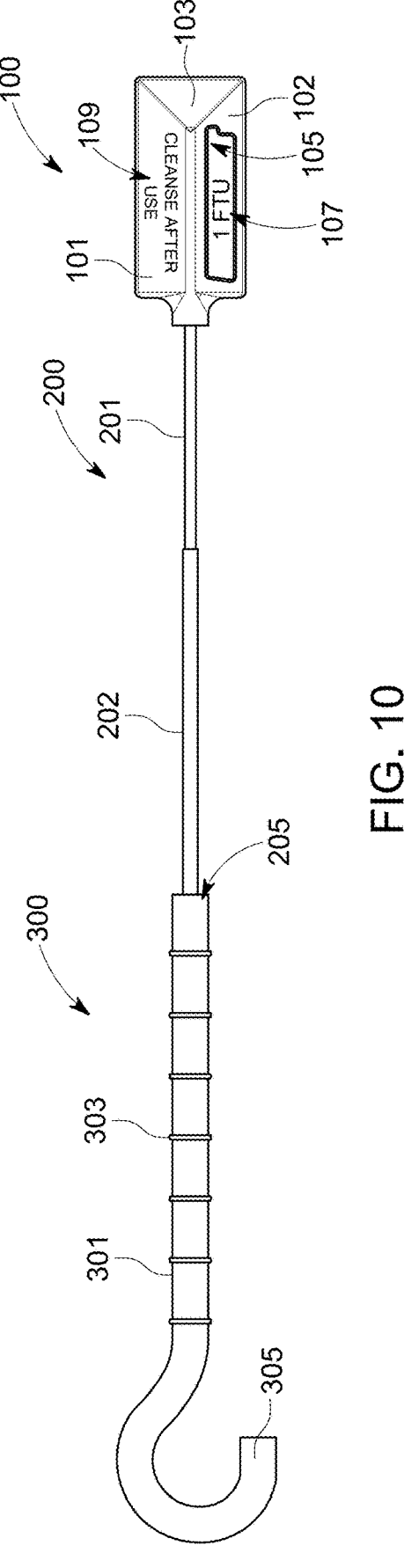
FIG. 10: shows an extended perspective view of the applicator, showing a silicone head having a rectangular, diamond surface and telescoping rod assembly, according to a preferred embodiment of the invention. In the embodiment shown, the handle includes raised fingertip unit markings for measuring the depth of lesions and further includes a base tool attached at its base which includes a hook.

FIG. 10 illustrates a preferred embodiment of the applicator with telescopic shaft 200 in its extended position which includes a base tool 305 in the form of a question mark which is attached to the proximal end of handle 300. Base tool/hook 305 provides a user the ability to hang or store the applicator from the hook.

Figure 11:
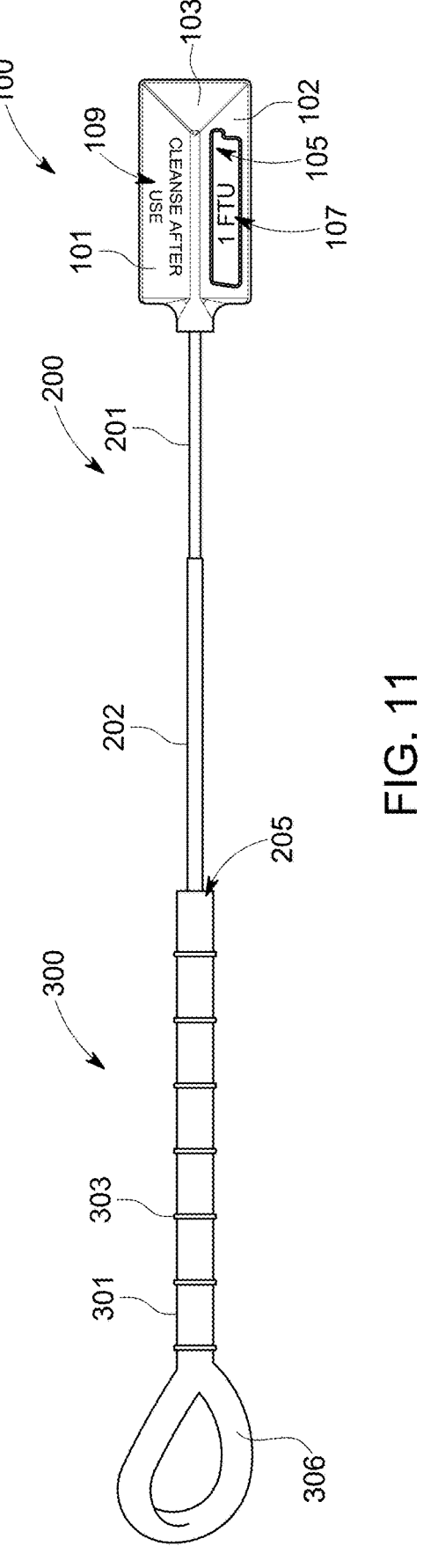
FIG. 11: shows an extended perspective view of the applicator, showing a silicone head having a rectangular, diamond surface and telescoping rod assembly, according to a preferred embodiment of the invention. In the embodiment shown, the handle includes raised fingertip unit markings for measuring the depth of lesions and further includes a base tool attached at its base which includes an oval shaped loop.

FIG. 11 illustrates a preferred embodiment of the applicator 10 with telescopic shaft 200 in its extended position which includes a base tool closed oval shaped loop 306 which is attached to the proximal end of handle 300. Loop 306 provides a user the ability to hang or otherwise secure applicator 10 using the opening of loop 306.

Figure 12:
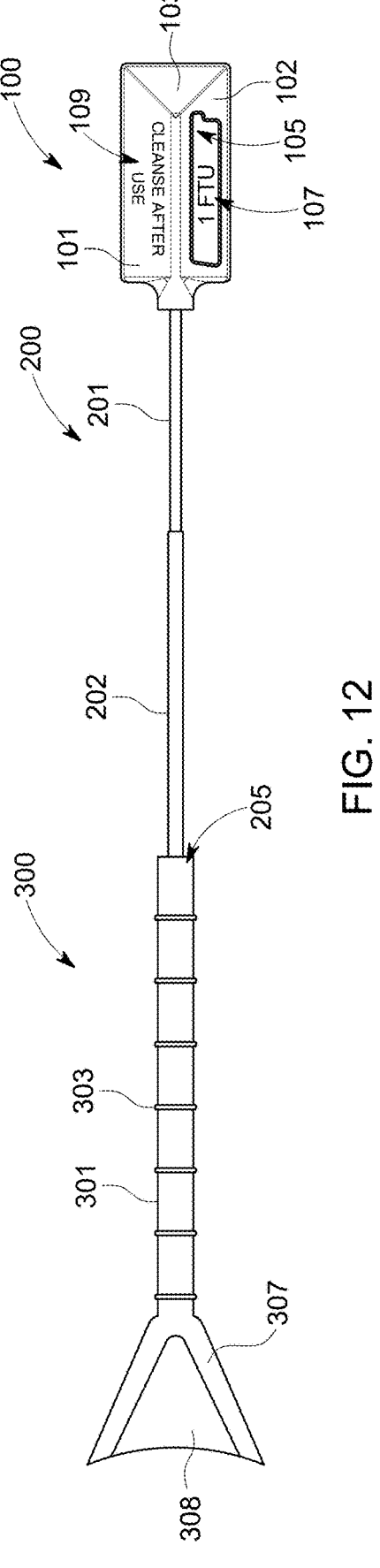
FIG. 12: shows an extended perspective view of the applicator, showing a silicone head having a rectangular, diamond surface and telescoping rod assembly, according to a preferred embodiment of the invention. In the embodiment shown, the handle includes raised fingertip unit markings for measuring the depth of lesions and further includes a base tool attached at its base which includes a palmate foot shaped top portion.

FIG. 12 illustrates a preferred embodiment of the applicator 10 with telescopic shaft 200 in its extended position which includes a base tool in the shape of a fin for applying a composition such as an ointment, lotion, gel or foam. The base tool is shaped similar to a palmate foot (the webbing of a duck foot) and includes a front thinner surface 308 and thicker rear edges 307. The fin shape provides for improved topical application when pressed against the skin because it conforms to the nature of the skin. The base tool provides dual functionality in addition to diamond shape head 100.

Figure 13:
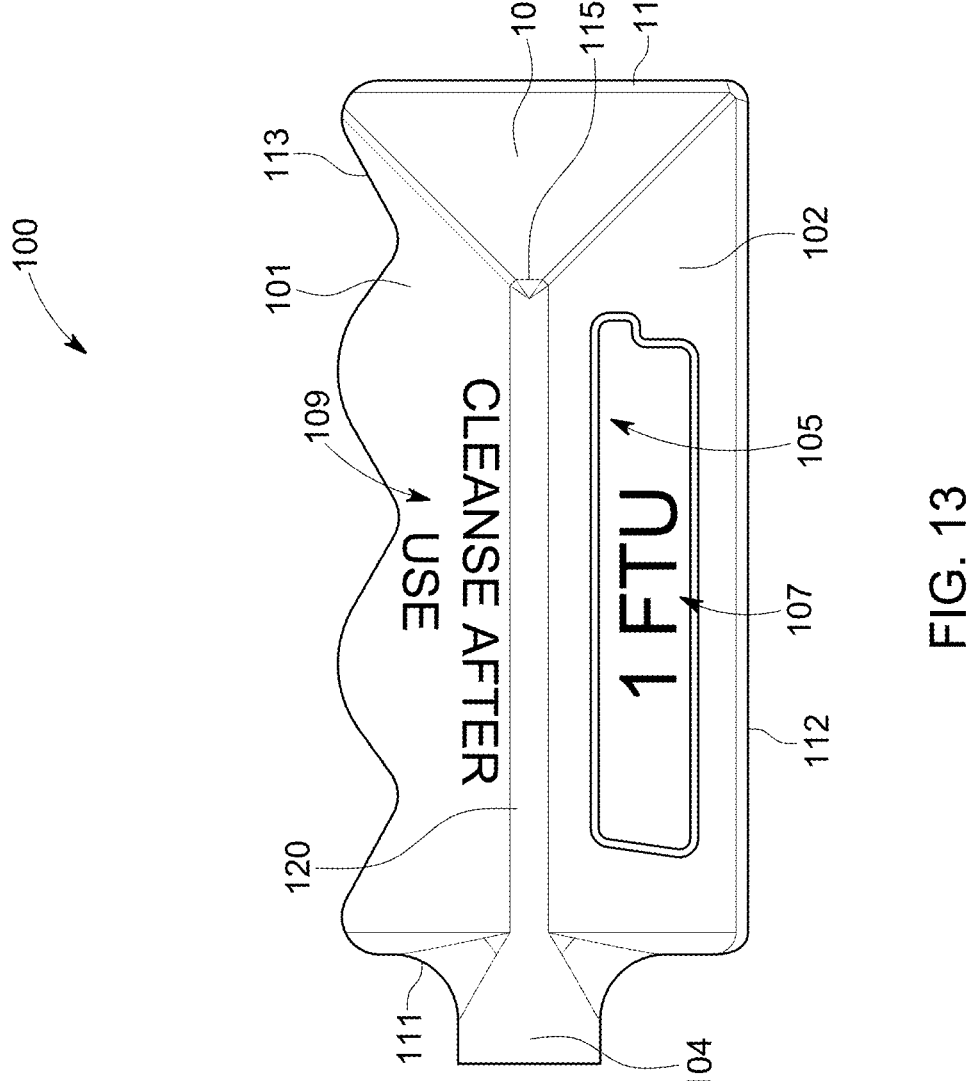
FIG. 13 illustrates a perspective view of an additional embodiment of the applicator head which includes a wavy length edge, which provides for ease of application to particular skin surfaces such as cracked, psoriatic or bumpy skin.

FIG. 13 illustrates a perspective view of an additional embodiment of the applicator head 100 which includes a wavy length edge 113, which is configured for ease of application to particular skin surfaces such as cracked, psoriatic or bumpy skin. In one embodiment, the edge includes a wavy, scalloped contour which includes a plurality of upward and downward curves. The waves are continuous, giving the edge a rippled profile.

The applicator as described herein can be made from various materials such as non-absorbent plastic, fiberglass, silicon, a metal or stainless steel. However, other materials are possible such as re-enforced durable silicone rubber and other molded plastics. In one embodiment, the applicator includes injection molded thermoplastic. The applicator can be molded from such materials (e.g., plastic, fiberglass, etc.) in a single material of any color by an injection molding process. In one embodiment, the head, handle and/or base tool can be made from one of these materials such as silicon, and the telescopic lens can be made from a different material such as metal or stainless steel.

The applicator of the current invention will find particular use for spreading of compositions for topical application. In some embodiments, the compositions are in the form a lotion, gel, cream, foam, or ointment. In some embodiments, the compositions are pharmaceutical compositions. Due to the particular configurations of the head (e.g., its multiple angles due to its diamond shape) as discussed herein, we have found that the applicator provides very easy and consistent spreading of various compositions. Other features of the applicator which are also discussed herein such as its extendable reach, additional functionalities, and rotation ability provide easy manipulation. The shape and smooth texture in various embodiments of the head also provide easy and quick cleaning of the applicator. In addition and where the applicator includes the embossed area for the finger-tip unit, the applicator will be useful for applications of pharmaceutical compositions where dosing is important.

Another advantage of applicator 10 is its convenience for extension to reach hard to reach areas such as the shoulders or back when it is extended as well as its convenience for storage when in its retracted state.

In a further aspect, the invention provides a kit that includes an applicator in accordance with the invention. Such kits can include various compositions such as creams, lotions, ointments, gels, foams and instructions for use of the applicator. The kit will typically include a box to fit each of the components of the kit.

In another aspect, the invention includes methods of applying to a subject such as a human by applying a spreadable composition to the skin or other external part of the body with an applicator in accordance with the invention for the treatment of a skin disorder. In some embodiments, the skin disorder is selected from the group of acne, eczema (atopic dermatitis), psoriasis, rosacea and contact dermatitis. In other embodiments, the skin disorder is selected from the group of warts, seborrheic dermatitis, hives, and various skin cancers.

In one preferred embodiment, the method of application includes the steps of: a) grasping the handle of an applicator as described herein, b) extending the telescopic shaft to a desired length, (c) dispensing an amount of medicament to the embossed area located on the surface of a wedged length end of the rectangular diamond head surface, and (c) manipulating the applicator to apply the medicament onto the bodily surface.

The invention claimed is:

1. An applicator which is used for spreading a composition onto the skin of a subject, comprising: a handle, a telescopic shaft and a rectangular, diamond surface head, wherein the handle is configured to completely contain the telescopic shaft when the shaft is in its retracted state and where the telescopic shaft can be extended longitudinally outward from a distal opening on the handle through a connection collar on the head when the applicator is in its extended state, wherein the rectangular, diamond surface head includes a center ridge projecting outward from the head and extending along the length of the head, the ridge physically separating three flexible wedge-like skin-contact spreading surfaces, including an inverted triangular spreading surface at a tip of the head and two opposing wedge-shaped spreading surfaces extending along opposite sides of the center ridge.

2. The applicator according to claim 1, wherein the rectangular, diamond surface head includes a serrated or rounded serrated edge along one of its lengths.

3. The applicator according to claim 1, wherein one of the opposing flexible wedge-like surfaces includes an embossed area is configured to hold an approximate volume of the composition for topical application to the skin.

4. The applicator according to claim 3, wherein the embossed area includes the embossed marking "1 FTU".

5. The applicator according to claim 4, wherein the 1 FTU embossed area is configured to measure one fingertip unit of composition.

6. The applicator according to claim 3, wherein an opposing flexible wedge-like surface includes a serrated edge, a rounded serrated edge, or a wavy edge.

7. The applicator according to claim 6, wherein the wavy edge is configured for easy spreading of the composition onto different surfaces of skin, wherein the surfaces are selected from a cracked, psoriatic or bumpy surface.

8. The applicator according to claim 3, wherein the head is composed of silicone.

9. The applicator according to claim 1, wherein the telescopic shaft of the applicator includes 2-5 sections, wherein each shaft section includes a diameter which is slightly wider than the diameter of the proximate shaft so that the smaller diameter shaft lodges firmly inside the larger diameter shaft.

10. The applicator according to claim 9, wherein the telescopic shaft is extendable and includes three sections which includes a base telescopic section which is configured to fit inside the handle of the applicator, a middle section of the telescopic shaft which is configured to fit inside the base shaft section, and a top shaft portion which is configured to fit inside the middle base section and which includes an upper portion that fits through a neck collar up to a pinnacle of an inverted triangle on the head of the applicator.

11. The applicator according to claim 10, wherein the base telescopic section is secured to the handle and the upper portion of the top portion shaft is secured to the central ridge extending along the length of the head.

12. The applicator according to claim 10, wherein the telescopic shafts are composed of stainless steel.

13. The applicator according to claim 10, wherein the handle of the applicator includes raised ridges which are spaced a distance of 1 cm along the length of the handle for use in measuring the size of lesions pre-m and post-treatment on the skin.

14. The applicator according to claim 10, wherein the handle is connected at its proximal end to a base tool which is in the shape of a question mark or hook or to an enclosed oval or loop for hanging and/or otherwise securing the applicator.

15. The applicator according to claim 10, wherein the handle is connected at its proximal end to a base tool which is in the shape of a fin, which when pressed against the skin conforms to the nature of the skin for improved topical application.

16. The applicator according to claim 15, where the fin includes a thinner front surface and thicker rear edges which provides for less irritation during topical application.

17. The applicator according to claim 10, wherein the applicator is part of a kit that includes (a) the applicator, (b) a composition in the form of a cream, lotion, gel, or foam, (c) instructions for use of the applicator, and (d) a box which is configured to fit the applicator and its components.

18. An applicator which is used for spreading a composition onto the skin of a subject, comprising: a rectangular, diamond surface head, wherein the rectangular, diamond surface head includes a center ridge projecting outward from the head and extending along the length of the head, the ridge physically separating three flexible wedge-like skin-contact spreading surfaces, including an inverted triangular spreading surface at a tip of the head and two opposing wedge-shaped spreading surfaces extending along opposite sides of the center ridge, a handle, wherein the handle includes raised ridges which are spaced along the length of the handle for use in measuring the size of lesions on the skin, and a telescopic shaft, wherein the telescopic shaft is extendable and includes three sections which includes a base telescopic section which is configured to fit inside the handle of the applicator, a middle shaft section which is configured to fit inside the base shaft section, and a top shaft portion which is configured to fit inside the middle shaft section and wherein the top shaft portion includes an upper portion that fits through a neck collar connected to the head up to a pinnacle of an inverted triangle on the head of the applicator, wherein the handle is configured to completely contain the telescopic shaft when the shaft is in its retracted state and where the telescopic shaft can be extended longitudinally outward from a distal opening on the handle through the connection collar on the head when the applicator is in its extended state.

19. The applicator according to claim 18, wherein the handle is connected at its proximal end to a base tool in the shape of a hook, a loop, a fin or a palmate foot.

20. A method of applying a composition to the skin or other external part of the body of a subject for the treatment of a skin disorder, which includes the steps of: a) grasping the handle of an applicator, wherein the applicator includes a handle, a telescopic shaft and a rectangular, diamond surface head, wherein the rectangular, diamond surface head includes a center ridge projecting outward from the head and extending along the length of the head, the ridge physically separating three flexible wedge-like skin-contact spreading surfaces, including an inverted triangular spreading surface at a tip of the head and two opposing wedge-shaped spreading surfaces extending along opposite sides of the center ridge and wherein the handle is configured to completely contain the telescopic shaft when the shaft is in its retracted state and where the telescopic shaft can be extended longitudinally outward from a distal opening on the handle through a connection collar on the head when the applicator is in its extended state, b) extending the telescopic shaft to a desired length, (c) dispensing an amount of the composition to fill an embossed area located on one of the opposing flexible wedge-like surfaces of the rectangular, diamond head surface, and (d) manipulating the applicator to apply the composition onto the bodily surface for the treatment of a skin disorder.

21. The method of claim 20, wherein the skin disorder is selected from the group of acne, eczema (atopic dermatitis), psoriasis, rosacea, contact dermatitis, and other dry skin conditions and other conditions such as but not limited to infections (viral, bacterial, yeast, and fungal), pruritic (itch), sunburn, and metabolic, autoimmune, inflammatory, and cancerous skin conditions.

\* \* \* \* \*